United States Patent
Mitsui et al.

(10) Patent No.: US 11,696,878 B2
(45) Date of Patent: Jul. 11, 2023

(54) OIL-IN-WATER TYPE EMULSIFIED COSMETIC

(71) Applicant: TOKIWA CORPORATION, Gifu (JP)

(72) Inventors: Daisuke Mitsui, Saitama (JP); Ryota Sakayama, Saitama (JP)

(73) Assignee: TOKIWA CORPORATION, Gifu (JP)

( * ) Notice: Subject to any disclaimer, the term of this patent is extended or adjusted under 35 U.S.C. 154(b) by 92 days.

(21) Appl. No.: 17/537,789

(22) Filed: Nov. 30, 2021

(65) Prior Publication Data
US 2022/0175630 A1 Jun. 9, 2022

(30) Foreign Application Priority Data
Dec. 9, 2020 (JP) .................. 2020-204035

(51) Int. Cl.
| | |
|---|---|
| *A61K 8/06* | (2006.01) |
| *A61K 8/55* | (2006.01) |
| *A61K 8/26* | (2006.01) |
| *A61K 8/73* | (2006.01) |
| *A61K 8/81* | (2006.01) |
| *A61Q 17/04* | (2006.01) |
| *A61Q 1/10* | (2006.01) |
| *A61Q 1/08* | (2006.01) |
| *A61K 8/28* | (2006.01) |
| *A61K 8/19* | (2006.01) |

(52) U.S. Cl.
CPC .............. *A61K 8/062* (2013.01); *A61K 8/19* (2013.01); *A61K 8/26* (2013.01); *A61K 8/28* (2013.01); *A61K 8/553* (2013.01); *A61K 8/73* (2013.01); *A61K 8/8188* (2013.01); *A61Q 1/08* (2013.01); *A61Q 1/10* (2013.01); *A61Q 17/04* (2013.01); *A61K 2800/30* (2013.01); *A61K 2800/43* (2013.01); *A61K 2800/48* (2013.01)

(58) Field of Classification Search
None
See application file for complete search history.

(56) References Cited

U.S. PATENT DOCUMENTS

2009/0093388 A1* 4/2009 Yamawaki ............ C07C 233/47
510/159

FOREIGN PATENT DOCUMENTS

JP 2013-136569 7/2013

* cited by examiner

*Primary Examiner* — Dominic Lazaro
(74) *Attorney, Agent, or Firm* — Greenblum & Bernstein, P.L.C.

(57) ABSTRACT

The oil-in-water type emulsified cosmetic includes: (A) a powder, (B) a water-soluble thickener, and (C) a surfactant, wherein the content of the component (A) is 1% to 30% by mass based on the total amount of the cosmetic, the component (A) contains (A1) an N-acyl acidic amino acid-treated powder, the component (C) contains (C1) a solid nonionic surfactant having a hydrophile-lipophile balance (HLB) value of less than 7 and (C2) a surfactant having an HLB value of 7 or greater, and the mass ratio [(C1):(C2)] between the component (C1) and the component (C2) is 1.5:1 to 30:1.

9 Claims, No Drawings

OIL-IN-WATER TYPE EMULSIFIED COSMETIC

TECHNICAL FIELD

The present invention relates to an oil-in-water type emulsified cosmetic.

BACKGROUND

Oil-in-water type emulsified cosmetics are highly appreciated because they give a fresh and refreshing sensation of use, and such cosmetics are widely used in makeup products, sunblocks, and the like.

Since the outer phase of oil-in-water type emulsified cosmetics is water, when a powder component is blended into such an emulsified cosmetic, it is common to use a hydrophilic powder in combination with a strongly hydrophilic surfactant. However, such cosmetics have a problem that the makeup film formed after application has inferior water resistance, and makeup deterioration occurs due to sweat and the like.

On the other hand, there has been proposed a sunblock cosmetic as an oil-in-water type emulsified cosmetic obtained by blending in a hydrophobized fine particle metal oxide powder in consideration of water resistance and perspiration resistance (see, for example, Japanese Unexamined Patent Publication No. 2013-136569).

SUMMARY

However, while color materials such as pigments are blended in as powder components in the case of makeup products, oil-in-water type emulsified cosmetics having hydrophobic pigments blended therein have a problem that the product appearance color and the applied color obtainable on the skin after application may look different, and the color in appearance is not likely to appropriately suggest the applied color to the consumers. On the other hand, oil-in-water type emulsified cosmetics having hydrophilic pigments blended in have a problem that since the water resistance of the makeup film is inferior as described above, the color tone changes upon contact with water.

It is an object of the present invention to provide an oil-in-water type emulsified cosmetic capable of reducing both the color difference between the product appearance color and the applied color obtainable on the skin, and the color difference produced when the emulsified cosmetic comes into contact with water.

In order to solve the above-described problems, there is provided an oil-in-water type emulsified cosmetic including: (A) a powder, (B) a water-soluble thickener, and (C) a surfactant, wherein the content of the component (A) is 1% to 30% by mass based on the total amount of the cosmetic, the component (A) contains (A1) an N-acyl acidic amino acid-treated powder, the component (C) contains: (C1) a solid nonionic surfactant having a hydrophile-lipophile balance (HLB) value of less than 7; and (C2) a surfactant having an HLB value of 7 or greater, and the mass ratio [(C1):(C2)] between the component (C1) and the component (C2) is 1.5:1 to 30:1.

According to the oil-in-water type emulsified cosmetic of the present invention, both the color difference between the product appearance color and the applied color obtainable on the skin, and the color difference occurring when the cosmetic is brought into contact with water can be reduced.

Incidentally, the inventors of the present invention speculate the reason why the above-described effects are obtained, as follows. First, with regard to an oil-in-water type emulsified cosmetic having a hydrophobic pigment blended in, it may be speculated that a color difference occurs between the product appearance color and the applied color obtainable on the skin because although the outer phase of the oil-in-water type emulsified cosmetic is water, when the cosmetic is applied on the skin, the outer phase undergoes phase inversion from water to oil in the middle. That is, it is speculated that pigments are dispersed in the inner phase in a product state, and when the pigments come to be dispersed in the outer phase as a result of phase inversion, this causes the color difference. As the oil-in-water type emulsified cosmetic of the present invention has the above-described configuration, (i) while the component (A1) is sufficiently dispersed in the inner phase, which is an oil phase, (ii) after application, the cosmetic can form a coating film that can sufficiently retain the component (A1). When a color material is used as the component (A1), it is speculated that since an appearance color close to the applied color in a product state is obtained as a result of the condition (i), a color difference attributable to the above-mentioned phase inversion is suppressed, and a color difference occurring when the cosmetic is brought into contact with water as a result of (ii), can be reduced.

Regarding the component (A1), the inorganic-organic balance (IOB) value of the treatment agent for the powder may be 2 to 5.

The oil-in-water type emulsified cosmetic of the present invention may include, as the component (C2), (C2-1) a nonionic surfactant having an HLB value of 7 or greater.

The oil-in-water type emulsified cosmetic of the present invention may include, as the component (C2), (C2-2) hydrogenated lecithin.

According to the present invention, an oil-in-water type emulsified cosmetic that can reduce both the color difference between the product appearance color and the applied color obtainable on the skin, and the color difference occurring when the cosmetic comes into contact with water, can be provided.

DETAILED DESCRIPTION

The oil-in-water type emulsified cosmetic of the present embodiment contains: (A) a powder component (may also be referred to as component (A)), (B) a water-soluble thickener (may also be referred to as component (B)), and (C) a surfactant (may also be referred to as component (C)).

<(A) Powder Component>

Regarding the powder component, any known powder used for cosmetics can be blended in, and examples include an extender powder and a coloring pigment. The powder can be used without being particularly limited in terms of the shape such as a spherical shape, a plate shape, or a needle shape; the particle size such as mist, fine particles, or pigment grade; particle structure such as porous or non-porous; and the like. Regarding the component (A), one kind thereof can be used alone, or two or more kinds thereof can be used in combination.

The oil-in-water type emulsified cosmetic of the present embodiment can contain, as the component (A), (A1) an N-acyl acidic amino acid-treated powder (hereinafter, also referred to as component (A1)). Regarding the component (A1), one kind thereof can be used alone, or two or more kinds thereof can be used in combination.

The acyl group in the N-acyl acidic amino acid may be an acyl group having 8 to 24 carbon atoms. The acidic amino acid in the N-acyl acidic amino acid may be glutamic acid or aspartic acid. The N-acyl acidic amino acid may be a sodium salt or a potassium salt.

Examples of the N-acyl acidic amino acid include N-stearoyl glutamic acid, N-lauroyl glutamic acid, N-myristoyl glutamic acid, and salts thereof. Specific examples include sodium stearoyl glutamate, disodium stearoyl glutamate, sodium lauroyl glutamate, disodium lauroyl glutamate, and potassium myristoyl glutamate.

The component (A1) may be such that a portion or the entirety of the surface of the base material powder is coated with an N-acyl acidic amino acid, the treatment method is not particularly limited, and the component (A1) can be obtained according to a known method such as a dry production method or a wet production method. The amount of the N-acyl acidic amino acid can be adjusted to 1 to 10 parts by mass with respect to 100 parts by mass of the base material powder and may be adjusted to 1 to 5 parts by mass.

Regarding the component (A1), commercially available products such as a NAI-treated powder (display name: 2Na stearoyl glutamate, disodium N-stearoyl-L-glutamate) manufactured by Miyoshi Kasei, Inc. can be used. Specific examples include NAI-titanium CR-50 (NAI-treated titanium oxide), NAI-Red R-516PS (NAI-treated red iron oxide), NAI-Yellow LL-100P (NAI-treated yellow iron oxide), and NAI-Black BL-100P (NAT-treated black iron oxide) (all trade names manufactured by Miyoshi Kasei, Inc.).

Regarding the component (A1), the IOB value of the treatment agent for the powder may be 2 to 5. According to the present specification, the IOB value is well known to represent the ratio of the inorganic value and the organic value, which are determined based on the organic conceptual diagram, and the IOB value represents the degree of polarity of an oily base and is represented by the following Formula (I).

$$IOB = \text{Inorganic value(IV)/organic value(OV)} \qquad (I)$$

Specifically, the IOB can be determined by the above-described Formula (I) according to "Prediction of Organic Compounds and Organic Conceptual Diagram", Fujita (Realm of Chemistry 11-10), 1957, p. 719-725, "Formulation and Design of Emulsification Based on Organic Conceptual Diagram", Nihon Emulsion Co., Ltd., Yaguchi, 1985, p. 98.

The IOB values (numerical values in the parentheses) of N-acyl acidic amino acids are shown below.

Sodium stearoyl glutamate (2.17), disodium stearoyl glutamate (3.26), sodium lauroyl glutamate (2.94), disodium lauroyl glutamate (4.41), potassium myristoyl glutamate (2.63).

When the component (A1) is a powder treated by two or more kinds of treatment agents, the sum of the values obtained by multiplying the IOB of each treatment agent by the blending amount of each treatment is divided by the total blending amount, and the resulting value is taken as the IOB value.

Regarding the base material powder for the component (A1), any base material powder that is usually used for cosmetic products can be used without particular limitations. Examples include an extender powder and a coloring pigment. Examples of the extender powder include an inorganic powder, a synthetic inorganic powder, an organic powder, a metal soap, and a synthetic polymer powder. More specific examples include glass powder, silicic anhydride, aluminum silicate, magnesium silicate, magnesium aluminum silicate, mica, synthetic phlogopite (synthetic mica), kaolin, sericite, synthetic sericite, talc, phlogopite, synthetic mica, silica, calcium carbonate, magnesium carbonate, aluminum oxide, boron nitride, silicon carbide, barium sulfate, zinc stearate, aluminum stearate, zinc myristate, polyethylene powder, urethane beads, polymethyl methacrylate, and organopolysiloxane elastomers. Examples of the coloring pigment include red iron oxide, yellow iron oxide, black iron oxide, cobalt oxide, chromium oxide, ultramarine blue, Prussian blue, titanium oxide, zinc oxide, microparticulate titanium oxide, pearl pigments (titanated mica, iron oxide-coated titanated mica, microparticulate titanium oxide-coated titanated mica, barium sulfate-coated titanated mica, fish scale guanine, bismuth oxychloride, aluminum flakes, and the like), organic pigments (Red No. 228, Red No. 226, Blue No. 404, Red No. 202, Yellow No. 4 aluminum lake, and the like), and natural colorants (carmine, safflower, and the like).

From the viewpoint of improving the color difference, the base material powder for the component (A1) may be a coloring pigment.

From the viewpoints of improvement in the color difference, satisfactory spreading, and absence of unevenness, the content of the component (A1) in the oil-in-water type emulsified cosmetic may be 1% by mass or more based on the total amount of the cosmetic and is preferably 3% by mass or more, and even more preferably 5% or more. Furthermore, the content of the component (A1) may be 30% by mass or less, may be 25% by mass or less, or may be 20% by mass or less, based on the total amount of the cosmetic.

Furthermore, from the viewpoints of improvement in color difference and usability, the content of the component (A1) may be 1% by mass or more based on the total amount of the component (A) and is preferably 10% by mass or more, and more preferably 20% by mass or more. Furthermore, the content of the component (A1) may be 100% by mass or less, may be 90% by mass or less, or may be 80% by mass or less, based on the total amount of the component (A).

The oil-in-water type emulsified cosmetic of the present embodiment can contain a powder other than the above-described component (A1). Regarding such a powder, any powder that is usually used for cosmetic products can be used without particular limitations. Examples include an extender powder and a coloring pigment Examples of the extender powder include an inorganic powder, a synthetic inorganic powder, an organic powder, a metal soap, and a synthetic polymer powder. More specific examples include glass powder, silicic anhydride, aluminum silicate, magnesium silicate, magnesium aluminum silicate, mica, synthetic phlogopite (synthetic mica), kaolin, sericite, synthetic sericite, talc, phlogopite, synthetic mica, silica, calcium carbonate, magnesium carbonate, aluminum oxide, boron nitride, silicon carbide, barium sulfate, zinc stearate, aluminum stearate, zinc myristate, polyethylene powder, urethane beads, polymethyl methacrylate, and organopolysiloxane elastomers. Examples of the coloring pigment include red iron oxide, yellow iron oxide, black iron oxide, cobalt oxide, chromium oxide, ultramarine blue, Prussian blue, titanium oxide, zinc oxide, microparticulate titanium oxide, pearl pigments (titanated mica, iron oxide-coated titanated mica, microparticulate titanium oxide-coated titanated mica, barium sulfate-coated titanated mica, fish scale guanine, bismuth oxychloride, aluminum flakes, and the like), organic pigments (Red No. 228, Red No. 226, Blue No. 404, Red No. 202, Yellow No. 4 aluminum lake, and the like), and natural colorants (carmine, safflower, and the like). These powders may be powders that have not been subjected to a surface treatment, or may have been subjected to a surface treatment for the purpose of enhancing usability, dispersibility, and the like. Examples of the surface treatment include a metal soap, a silicone compound, a fluorine compound, a surfactant, and an amino acid compound.

From the viewpoint of imparting functionality for the purpose of makeup such as the cover power, color development, and ultraviolet cutting, the content of the component (A) in the oil-in-water type emulsified cosmetic may be 1% by mass or more based on the total amount of the cosmetic and is preferably 3% by mass or more, and more preferably 5% by mass or more. Furthermore, from the viewpoint of usability such as uniformity of the makeup film and satisfactory spreading, the content of the component (A) may be 30% by mass or less based on the total amount of the cosmetic and is preferably 25% by mass or less, and more preferably 20% by mass or less.

<(B) Water-Soluble Thickener>

Regarding the water-soluble thickener, any known water-soluble thickener used for cosmetics can be blended in, and for example, a polysaccharide-based thickener, a clay mineral, an acrylic acid amide copolymer, or a cellulose-based thickener can be used. Regarding the component (B), one kind thereof can be used alone, or two or more kinds thereof can be used in combination.

Examples of the polysaccharide-based thickener include pectin, guar gum, xanthan gum, carrageenan, gellan gum, gum arabic, and locust bean gum.

Examples of the clay mineral include (Al/Mg) silicate, (Na/Mg) silicate, bentonite, Al silicate, and Na silicate.

Examples of the acrylic acid amide copolymer include polyacrylamide, a (hydroxyethyl acrylate-Na acryloyldimethyl taurine) copolymer, a (Na acrylate-Na acryloyldimethyl taurine) copolymer, an (ammonium acryloyldimethyl taurine-VP) copolymer, and an (ammonium acryloyldimethyl taurine-beheneth-25 methacrylate) cross-polymer.

Examples of the cellulose-based thickener include methyl cellulose, ethyl cellulose, carboxymethyl cellulose, cellulose gum (sodium carboxymethyl cellulose), hydroxyethyl cellulose, hydroxypropyl cellulose, and hydroxypropyl methylcellulose.

From the viewpoints of the absence of color unevenness (uniformity of the coating film) and storage stability, the oil-in-water type emulsified cosmetic of the present embodiment may include, as the component (B), one or more selected from the group consisting of xanthan gum, gum arabic, guar gum, tamarind gum, native gellan gum, (Al/Mg) silicate, bentonite, Al silicate, Na silicate, (Na/Mg) silicate, (Na/Mg) silicate, a (hydroxyethyl acrylate-Na acryloyldimethyl taurine) copolymer, a (Na acrylate-Na acryloyldimethyl taurine) copolymer, an (ammonium acryloyldimethyl taurine-VP) copolymer, and polyacrylamide.

Furthermore, from the viewpoints of the absence of color unevenness (uniformity of the coating film) and further improving storage stability, the oil-in-water type emulsified cosmetic of the present embodiment may include, as the component (B), two or more selected from the group consisting of a (Na acrylate-Na acryloyldimethyl taurine) copolymer, xanthan gum, and (Al/Mg) silicate.

From the viewpoint of satisfactorily dispersing the component (A1), the content of the water-soluble thickener in the oil-in-water type emulsified cosmetic of the present embodiment may be 0.01% to 5% by mass, may be 0.05% to 4% by mass, and may be 0.1% to 3% by mass, based on the total amount of the cosmetic.

<(C) Surfactant>

Examples of the surfactant include an anionic surfactant, a cationic surfactant, an amphoteric surfactant, and a nonionic surfactant. Regarding the component (C), one kind thereof can be used alone, or two or more kinds thereof can be used in combination.

The oil-in-water type emulsified cosmetic of the present embodiment can contain (C1) a solid nonionic surfactant having an HLB value of less than 7 (hereinafter, also referred to as component (C1)) and (C2) a surfactant having an HLB value of 7 or greater (hereinafter, also referred to as component (C2)) as the component (C). Regarding each of the component (C1) and the component (C2), one kind thereof can be used alone, or two or more kinds thereof can be used in combination.

The HLB value can be determined based on the calculation formula described in "Technology of Emulsification•Solubilization", Kougakutosho, Ltd. (Sho-59-5-20), p. 8-12. Furthermore, when it is said that the nonionic surfactant is solid, it means that the nonionic surfactant does not exhibit fluidity at 25° C. and does not change into an indeterminate form.

Examples of the component (C1) include glycerin fatty acid esters such as glyceryl stearate (HLB 3); sorbitan fatty acid esters such as sorbitan palmitate (HLB 6.7), sorbitan stearate (HLB 4.7), and sorbitan sesquistearate (HLB 4.2); and polyethylene glycol fatty acid esters such as PEG-2 stearate (HLB 4.0).

Regarding the component (C1), the HLB value may be 1 or greater and less than 7, may be 2 to 6, or may be 3 to 5.

Examples of the component (C2) include: (C2-1) a nonionic surfactant having an HLB value of 7 or greater (hereinafter, also referred to as component (C2-1)) and (C2-2) hydrogenated lecithin (hereinafter, also referred to as component (C2-2)). Regarding each of the component (C2-1) and the component (C2-2), one kind thereof can be used alone, or two or more kinds thereof can be used in combination.

Examples of the component (C2-1) include polyoxyethylene hardened castor oils such as PEG-40 hydrogenated castor oil (HLB 12.5) and PEG-60 hydrogenated castor oil (HLB 14); polyoxyethylene sorbitan fatty acid esters such as polyoxyethylene sorbitan (20 E.O.) monooleate (HLB 15) and polyoxyethylene sorbitan (20 E.O.) monostearate (HLB 14.9); polyoxyethylene sorbite fatty acid esters such as polyoxyethylene sorbite tetraoleate (HLB: 11.5); polyoxyethylene glycerin fatty acid esters such as PEG-20 glyceryl stearate (HLB 14), PEG-15 glyceryl stearate (HLB 13.5), PEG-10 glyceryl isostearate (HLB 10), and PEG-30 glyceryl isostearate (HLB 15); polyethylene glycol fatty acid esters such as PEG-12 laurate (HLB 13.7); sorbitan fatty acid esters such as coconut fatty acid sorbitan (HLB 12); and polyglycerin fatty acid esters such as polyglyceryl-10 stearate (HLB 12).

Regarding the component (C2-1), the HLB value may be 7 to 18, may be 9 to 16, or may be 10 to 15.

Regarding the component (C2-2), the HLB value may be 7 to 18, may be 7 to 15, or may be 7 to 11.

From the viewpoint of reducing the color difference between the product appearance color and the applied color obtainable on the skin, and the color difference occurring when the cosmetic comes into contact with water, the mass ratio [(C1):(C2)] between the component (C1) and the component (C2) may be 1.5:1 to 30:1, may be 2:1 to 10:1, or may be 2:1 to 3.9:1.

When the component (C1) and the component (C2-1) are combined, the mass ratio of those components [(C1):(C2-1)] may be 1.5:1 to 25:1 or may be 2:1 to 15:1.

When the component (C1) and the component (C2-2) are combined, the mass ratio of those components [(C1):(C2-2)] may be 1.5:1 to 30:1 or may be 2:1 to 20:1.

The content of the component (C) in the oil-in-water type emulsified cosmetic of the present embodiment may be 0.1% to 9% by mass, may be 1% to 5% by mass, or 1% to 3% by mass, based on the total amount of the cosmetic.

Furthermore, from the viewpoint of storage stability, the sum of the contents of the component (C1) and the component (C2) may be 50% by mass or more, 60% by mass or more, 70% by mass or more, or 80% by mass or more, based on the total amount of the component (C). The sum of the contents of the component (C1) and the component (C2) may be 100% by mass or less, 95% by mass or less, or 90% by mass or less, based on the total amount of the component (C).

The oil-in-water type emulsified cosmetic of the present embodiment can further contain (D) an oily component (hereinafter, also referred to as component (D)). Regarding the component (D), one kind thereof can be used alone, or two or more kinds thereof can be used in combination.

Examples of the component (D) include oils and fats, waxes, a hydrocarbon, an ester oil, a higher alcohol, a higher fatty acid, a silicone oil, and an oil-soluble ultraviolet absorber. Regarding the component (D), one kind thereof can be used alone, or two or more kinds thereof can be used in combination.

Examples of the oils and fats include solid oils and fats such as hardened castor oil, hydrogenated jojoba oil, palm oil, and wood wax; and liquid oils and fats such as jojoba seed oil, sunflower seed oil, olive oil, castor oil, macadamia nut oil, camellia oil, rapeseed oil, linseed oil, and triglycerin.

Examples of the waxes include beeswax, carnauba wax, candelilla wax, rice bran wax, sunflower seed wax, bran wax, whale wax, and lanolin.

Examples of the hydrocarbon include polyethylene wax, microcrystalline wax, Fischer-Tropsch wax, ceresin, petrolatum, liquid paraffin, squalane, and mineral oil.

Examples of the ester oil include glyceryl tribehenate, a cholesterol fatty acid ester, diisostearyl malate, isopropyl myristate, cetyl 2-ethylhexanoate, isopropyl palmitate, ethylhexyl palmitate, glyceryl tricaprylate-caprate, neopentyl glycol dicaprate, glyceryl tri-2-ethylhexanoate, polyglyceryl triisostearate, dipentaerythrityl tetra(hydroxystearate-isostearate), neopentyl glycol di-2-ethylhexanoate, triethylhexanoin, and a dimer acid ester.

Examples of the higher alcohol include stearyl alcohol, behenyl alcohol, cetyl alcohol, cetostearyl alcohol, oleyl alcohol, octyldodecanol, and isostearyl alcohol.

Examples of the higher fatty acid include stearic acid, oleic acid, myristic acid, palmitic acid, isostearic acid, behenic acid, linoleic acid, and linolenic acid.

Examples of the silicone oil include dimethylpolysiloxane, methylphenyl polysiloxane, octamethylcyclotetrasiloxane, decamethylcyclopentasiloxane, and methyltrimethicone.

From the viewpoints of usability and water resistance, the sum of the contents of the component (D) in the oil-in-water type emulsified cosmetic of the present embodiment may be 1% to 40% by mass, may be 2% to 30% by mass, or 3% to 20% by mass, based on the total amount of the cosmetic.

From the viewpoint of imparting freshness and satisfactory spreading, the content of water in the oil-in-water type emulsified cosmetic of the present embodiment may be 1% to 95% by mass, may be 10% to 90% by mass, may be 20% to 80% by mass, or may be 30% to 70% by mass, based on the total amount of the cosmetic.

<Other Components>

The oil-in-water type emulsified cosmetic of the present embodiment can include components other than the above-mentioned components. Regarding the other components, components that are usually used for cosmetics, for example, aqueous components such as a humectant and a lower alcohol; an ultraviolet absorber, an anti-foaming agent, an antiseptic agent, vitamins, a beauty component, an antioxidant, and a fragrance can be appropriately blended in as necessary, to the extent that does not impair the effects of the present invention.

Examples of the humectant include polyhydric alcohols such as 1,3-butylene glycol (BG), dipropylene glycol (DPG), glycerin, 1,2-pentanediol, sorbitol, and mannitol. These can be used singly, or two or more kinds thereof can be used in combination.

Examples of the lower alcohol include ethanol, propyl alcohol, isopropyl alcohol, and isobutyl alcohol. These can be used singly, or two or more kinds thereof can be used in combination.

In the oil-in-water type emulsified cosmetic of the present embodiment, the content of the component (A) may be 1% to 30% by mass based on the total amount of the cosmetic, the component (A) may contain the component (A1), the component (C) may contain the component (C1) and the component (C2), and the mass ratio [(C1):(C2)] between the component (C1) and the component (C2) may be 1.5:1 to 30:1.

Such an oil-in-water type can maintain sufficient storage stability even in a case where a component having a PEG (polyethylene glycol) group, which is effective for stabilization of the oil-in-water type emulsified cosmetic, is substantially not blended in. The component having a PEG group refers to a compound including the structure of [—(CH$_2$CH$_2$O)$_n$-] obtained by addition polymerizing ethylene oxide (EO modification), and a derivative thereof.

The oil-in-water type emulsified cosmetic of the present embodiment may be a cosmetic that substantially does not include a component having a PEG group, from the viewpoint of low skin stimulation. Incidentally, the phrase "substantially does not include a component having a PEG group" means that a component having a PEG group is not separately blended in, and it is not intended to exclude even a trace amount of a PEG group-containing component included in each blending component (carry-over component). The content of the carry-over component in the oil-in-water type emulsified cosmetic may be 0.1% by mass or less based on the total amount of the cosmetic.

With regard to the oil-in-water type emulsified cosmetic of the present embodiment, from the viewpoints of the usability and storage stability, the viscosity at 25° C. may be 500 to 300000 mPa·s, may be 1000 to 200000 mPa·s, or may be 2000 to 100000 mPa·s.

The above-described viscosity means a value measured for a sample at 25° C. using a Brookfield type viscometer (BM type) or a Brookfield type viscometer (BH type) under the following conditions.

250 to 2500 mPa·s: BM type, rotor No. 2, speed of rotation 12 rpm 1000 to 10000 mPa·s: BM type, rotor No. 3, speed of rotation 12 rpm 5000 to 50000 mPa·s: BM type rotor No. 4, speed of rotation 12 rpm 50000 to 400000 mPa·s: BH type, rotor No. 7, speed of rotation 10 rpm Examples of the use applications for the oil-in-water type emulsified cosmetic of the present embodiment include makeup cosmetics such as blusher, eyeshadow, foundation, lipstick, concealer, highlighter, makeup base, eyeliner, and eyebrow; cosmetics for body such as sunscreen (sunblock); and hair care cosmetics such as hair wax and hair color.

[Method for Producing Oil-In-Water Type Emulsified Cosmetic]

Regarding the method for producing the oil-in-water type emulsified cosmetic according to the present embodiment, for example, the cosmetic can be obtained by mixing and emulsifying the above-mentioned component (A), component (B), component (C), and component (D), and optionally other components.

Regarding the order of mixing, for example, emulsification may be carried out by mixing, with stirring, an oil phase obtainable by mixing the component (A), component (C1), and component (D) into an aqueous phase obtainable by mixing the component (B), component (C2), and water or an aqueous component. Furthermore, the component (C) can be mixed into the aqueous phase when the component is a hydrophilic surfactant, and into the oil phase when the component is an oleophilic surfactant. The temperature at the time of preparing the oil phase is preferably a temperature at which the component (C) and the component (D) melt. The temperature at the time of preparing the aqueous phase is preferably a temperature at which the component (B) and the component (C) melt.

EXAMPLES

Hereinafter, the present invention will be described in more detail by way of Examples; however, the technical scope of the present invention is not intended to be limited by these Examples.

Production of Oil-In-Water Type Emulsified Cosmetic

Examples 1 to 24 and Comparative Examples 1 to 7

Oil-in-water type emulsified cosmetics (foundations) were prepared by the following production method according to the formulations shown in Tables 1 to 4 (the value of a blending amount represents the content (% by mass) based on the total amount of the cosmetic).

Meanwhile, the details of the raw materials in Tables 1 to 4 and of Examples 25 to 27 are as follows.

<Component (A)>

For each NAI-treated powder, NAI series manufactured by Miyoshi Kasei, Inc. were used. Furthermore, for each dimethicone-treated powder, SA series manufactured by Miyoshi Kasei, Inc. were used.

<Component (B)>

Copolymer-1: (Hydroxyethyl acrylate/Na acryloyldimethyl taurine) copolymer

Copolymer-2: (Ammonium acryloyldimethyl taurine/VP) copolymer

<Component (C)>

Glyceryl stearate: HLB 3, solid
Sorbitan stearate: HLB 4.7, solid
Polysorbate 80: HLB 15
PEG-60 hydrogenated castor oil: HLB 14
PEG-10 glyceryl isostearate: HLB 10
Coconut fatty acid sorbitan: HLB 12
Polyglyceryl stearate 10: HLB 12
Hydrogenated lecithin: HLB 7.9
Sorbitan isostearate: HLB 5, liquid
Sorbitan sesquioleate: HLB 3.7, liquid <Production Method>

Component (A), component (C1), and component (D) were mixed and heated to 90° C. to melt, the mixture was made uniform, and this was used as an oil phase. Next, aqueous components including component (B), component (C2), and water were mixed and heated to 90° C. to melt, and the mixture was used as an aqueous phase. Emulsification was carried out by adding the oil phase into the aqueous phase at 90° C. with stirring, and by cooling, an oil-in-water type emulsified cosmetic (foundation) was obtained. Meanwhile, sorbitan isostearate of Comparative Example 6 and sorbitan sesquioleate of Comparative Example 7 were mixed into the oil phase.

The oil-in-water type emulsified cosmetics thus obtained were subjected to evaluation for each item based on the following evaluation methods. The results are shown in Table 5.

<Color Difference of Appearance Color and Coating Film>

0.5 mg/cm$^2$ of each of the cosmetics was weighed and taken on artificial skin, the cosmetic was uniformly applied with a finger capped with a finger stall, and the cosmetic was dried at room temperature to form a coating film. The color difference ΔE* between the bulk and a coating film of the cosmetic was measured using a color difference meter CR-400 (manufactured by Konica Minolta, Inc.), and the color difference between the appearance color and the coating film color was determined according to the following evaluation criteria.

[Determination Criteria]
A: ΔE*<1.5
B: 1.5≤ΔE*<2
C: 2≤ΔE*<2.5
D: 2.5≤ΔE*

<Color Difference after Contact with Water>

0.5 mg/cm$^2$ of each of the cosmetics was weighed and taken on artificial skin, the cosmetic was uniformly applied with a finger capped with a finger stall, and the cosmetic was dried at room temperature to form a coating film. 5 mg of water was squirted on this coating film with a dropper, and water was wiped out. The color difference ΔE* between the coating film and the coating film after wiping out water was measured using a color difference meter CR-400 (manufactured by Konica Minolta, Inc.), and the color difference after contact with water was evaluated according to the following evaluation criteria.

[Determination Criteria]
A: ΔE*<1.5
B: 1.5≤ΔE*<2.0
C: 2.0≤ΔE*

<Water Resistance (Contact Angle)>

0.5 mg/cm$^2$ of each of the cosmetics was weighed and taken on artificial skin, the cosmetic was uniformly applied with a finger capped with a finger stall, and the cosmetic was dried at room temperature to form a coating film. 1 to 2 ml of water was dropped on this coating film, and after 1 minute, an image of this was captured from right beside with a camera to obtain an image. From this image, the contour shape of the liquid droplet was analyzed, the contact angle was calculated, and water resistance was evaluated according to the following determination criteria. The contact angle means an angle formed by the water droplet and the coating film and means a value obtained by a tangent line method (Tangent 1).

[Determination Criteria]
A: The contact angle is 70° or larger.
B: The contact angle is 40° or larger and less than 70°.
C: The contact angle is less than 40°.

<Usability (Cover Power, Satisfactory Spreading, and Absence of Unevenness)>

Ten expertise panels for cosmetics evaluation were asked to use each of the cosmetics of Examples and Comparative Examples, and usability was evaluated from the viewpoints of the cover power, satisfactory spreading, and the absence of unevenness (uniformity of coating film). Regarding the evaluation of usability, a 5-grade evaluation was carried out according to the following evaluation criteria, rating scores were assigned for each sample, and the average score of the rating scores obtained from all the panels was determined according to the following determination criteria.

[Rating Score: Evaluation Criteria]
Score 5: Highly satisfactory
Score 4: Satisfactory
Score 3: Ordinary
Score 2: Slightly poor
Score 1: Poor

[Determination Criteria (Average Score of Rating Scores)]
A: 4 or more
B: 3 or more and less than 4
C: 2 or more and less than 3
D: Less than 2

<Storage Stability>

The cosmetics were stored for one month at room temperature. The state of the cosmetic after storage was visually inspected, and the storage stability was evaluated according to the following determination criteria.

[Determination Criteria]
A: No change.
B: Syneresis or separation is observed.

TABLE 1

|  |  |  | Example 1 | Example 2 | Example 3 | Example 4 | Example 5 | Example 6 | Example 7 |
|---|---|---|---|---|---|---|---|---|---|
| (A) Powder component | (A1) | NAI-treated titanium oxide | 6.5 | 10.0 | 1.5 | 6.5 | 6.5 | 6.5 | 6.5 |
|  |  | NAI-treated yellow iron oxide | 1.2 | 1.8 | 0.3 | 1.2 | 1.2 | 1.2 | 1.2 |
|  |  | NAI-teated red iron oxide | 0.16 | 0.24 | — | 0.16 | 0.16 | 0.16 | 0.16 |
|  |  | NAI-teated mica | — | 4.0 | — | — | — | — | — |
|  |  | Stearic acid-treated microparticulate titanium oxide | 10.0 | 10.0 | 10.0 | 10.0 | 10.0 | 10.0 | 10.0 |
| (B) Water-soluble thickener |  | (Al/Mg) silicate | 3.6 | 3.6 | 3.6 | 3.6 | 3.6 | 3.6 | 3.6 |
|  |  | Xanthan gum | 0.9 | 0.9 | 0.9 | 0.9 | 0.9 | 0.9 | 0.9 |
| (C) Surfactant | (C1) | Glyceryl stearate | 1.0 | 1.0 | 1.0 | — | 0.6 | 1.8 | 2.5 |
|  |  | Sorbitan stearate | — | — | — | 1.0 | — | — | — |
|  | (C2) | Hydrogenated lecithin | 0.3 | 0.3 | 0.3 | 0.3 | 0.3 | 0.2 | 0.1 |
| (D) Oily component |  | Cetyl ethylhexanoate | 14.5 | 14.5 | 14.5 | 14.5 | 14.5 | 14.5 | 14.5 |
|  |  | Water | Balance | Balance | Balance | Balance | Balance | Balance | Balance |
|  |  | 1,3-Butylene glycol | 3 | 3 | 3 | 3 | 3 | 3 | 3 |
|  |  | pH adjusting agent | Proper quantity | Proper quantity | Proper quantity | Proper quantity | Proper quantity | Proper quantity | Proper quantity |
|  |  | Antiseptic agent | Proper quantity | Proper quantity | Proper quantity | Proper quantity | Proper quantity | Proper quantity | Proper quantity |
|  |  | Total (parts by mass) | 100 | 100 | 100 | 100 | 100 | 100 | 100 |
|  |  | Powder component (% by mass) | 17.9 | 26.0 | 11.8 | 17.9 | 17.9 | 17.9 | 17.9 |
|  |  | (C1):(C2) | 3.33:1 | 3.33:1 | 3.33:1 | 3.33:1 | 2:1 | 9:1 | 25:1 |

TABLE 2

|  |  |  | Example 8 | Example 9 | Example 10 | Example 11 | Example 12 | Example 13 | Example 14 | Example 15 |
|---|---|---|---|---|---|---|---|---|---|---|
| (A) Powder component | (A1) | NAI-treated titanium oxide | 6.5 | 6.5 | 6.5 | 6.5 | 9.0 | 12.0 | 10.0 | 1.5 |
|  |  | NAI-treated yellow iron oxide | 1.2 | 1.2 | 1.2 | 1.2 | 1.3 | 1.2 | 1.8 | 0.3 |
|  |  | NAI-treated red iron oxide | 0.16 | 0.16 | 0.16 | 0.16 | 0.16 | 0.16 | 0.24 | — |
|  |  | NAI-treated black iron oxide | — | — | — | — | 0.10 | 0.10 | — | — |
|  |  | NAI-treated mica | — | — | — | — | — | — | 4.0 | — |
|  |  | Stearic acid-treated microparticulate titanium oxide | 10.0 | 10.0 | 10.0 | 10.0 | 5.0 | — | 10.0 | 10.0 |

TABLE 2-continued

|  |  |  | Example 8 | Example 9 | Example 10 | Example 11 | Example 12 | Example 13 | Example 14 | Example 15 |
|---|---|---|---|---|---|---|---|---|---|---|
| (B) Water-soluble thickener | | (Al/Mg) silicate | 1.0 | 1.0 | 1.0 | 1.0 | 1.0 | 1.0 | 1.0 | 1.0 |
| | | Xanthan gum | 0.25 | 0.25 | 0.25 | 0.25 | 0.25 | 0.25 | 0.25 | 0.25 |
| | | Copolymer-1 | 0.5 | 0.5 | 0.5 | 0.5 | 0.5 | 0.5 | 0.5 | 0.5 |
| (C) Surfactant | (C1) | Glyceryl stearate | 1.0 | — | 1.0 | 1.0 | 2.0 | 2.0 | 1.0 | 1.0 |
| | | Sorbitan stearate | — | 1.0 | — | — | — | — | — | — |
| | (C2) | Polysorbate 80 | 0.1 | 0.1 | — | — | — | — | 0.1 | 0.1 |
| | | PEG-60 hydrogenated castor oil | — | — | 0.1 | — | — | — | — | — |
| | | PEG-10 glyceryl isostearate | — | — | — | 0.1 | — | — | — | — |
| | | Coconut fatty acid sorbitan | — | — | — | — | 0.1 | — | — | — |
| | | Polyglyceryl-10 stearate | — | — | — | — | — | 0.1 | — | — |
| (D) Oily component | | Cetyl ethylhexanoate | 14.5 | 14.5 | 14.5 | 14.5 | 5.0 | 5.0 | 14.5 | 14.5 |
| | | Mineral oil | — | — | — | — | 5.0 | 10.0 | — | — |
| | | Water | Balance | Balance | Balance | Balance | Balance | Balance | Balance | Balance |
| | | 1,3-Butylene glycol | 3 | 3 | 3 | 3 | 3 | 3 | 3 | 3 |
| | | pH adjusting agent | Proper quantity | Proper quantity | Proper quantity | Proper quantity | Proper quantity | Proper quantity | Proper quantity | Proper quantity |
| | | Antiseptic agent | Proper quantity | Proper quantity | Proper quantity | Proper quantity | Proper quantity | Proper quantity | Proper quantity | Proper quantity |
| | | Total (parts by mass) | 100 | 100 | 100 | 100 | 100 | 100 | 100 | 100 |
| | | Powder component (% by mass) | 17.9 | 17.9 | 17.9 | 17.9 | 15.6 | 13.5 | 26.0 | 11.8 |
| | | (C1):(C2) | 10:1 | 10:1 | 10:1 | 10:1 | 20:1 | 20:1 | 10:1 | 10:1 |

TABLE 3

|  |  |  | Example 16 | Example 17 | Example 18 | Example 19 | Example 20 | Example 21 | Example 22 | Example 23 | Example 24 |
|---|---|---|---|---|---|---|---|---|---|---|---|
| (A) Powder component | (A1) | NAI-treated titanium oxide | 6.5 | 6.5 | 6.5 | 6.5 | 6.5 | 6.5 | 6.5 | 6.5 | 6.5 |
| | | NAI-treated yellow iron oxide | 1.2 | 1.2 | 1.2 | 1.2 | 1.2 | 1.2 | 1.2 | 1.2 | 1.2 |
| | | NAI-treated red iron oxide | 0.16 | 0.16 | 0.16 | 0.16 | 0.16 | 0.16 | 0.16 | 0.16 | 0.16 |
| | | NAI-treated black iron oxide | — | — | — | — | — | — | — | — | — |
| | | Stearic acid-treated microparticulate titanium oxide | 10.0 | 10.0 | 10.0 | 10.0 | 10.0 | 10.0 | 10.0 | 10.0 | 10.0 |
| (B) Water-soluble thickener | | (Al/Mg) silicate | 1.0 | 1.0 | 1.0 | 1.0 | 1.0 | 1.0 | — | — | — |
| | | (Na/Mg) silicate | — | — | — | — | — | — | — | 1.0 | — |
| | | Bentonite | — | — | — | — | — | — | — | — | 1.0 |
| | | Copolymer-1 | 0.25 | 0.25 | 0.25 | 0.25 | 0.25 | 0.25 | 1.50 | — | — |
| | | Copolymer-2 | 0.5 | 0.5 | 0.5 | 0.5 | 0.5 | 0.5 | — | — | — |
| | | Polyacrylamide | — | — | — | — | — | — | — | 1.0 | — |
| (C) Surfactant | (C1) | Glyceryl stearate | 0.6 | 2.5 | 4.0 | 0.8 | 3.0 | 4.5 | 1.0 | 1.0 | 1.0 |
| | (C2) | Polysorbate 80 | 0.1 | 0.1 | 1.0 | 0.2 | 2.0 | 0.2 | 0.1 | 0.1 | 0.1 |
| (D) Oily component | | Cetyl ethylhexanoate | 14.5 | 14.5 | 14.5 | 14.5 | 14.5 | 14.5 | 14.5 | 14.5 | 14.5 |
| | | Water | Balance | Balance | Balance | Balance | Balance | Balance | Balance | Balance | Balance |
| | | 1,3-Butylene glycol | 3 | 3 | 3 | 3 | 3 | 3 | 3 | 3 | 3 |
| | | pH adjusting agent | Proper quantity | Proper quantity | Proper quantity | Proper quantity | Proper quantity | Proper quant | Proper quantity | Proper quantity | Proper quantity |
| | | Antiseptic agent | Proper quantity | Proper quantity | Proper quantity | Proper quantity | Proper quantity | Proper quantity | Proper quantity | Proper quantity | Proper quantity |
| | | Total (parts by mass) | 100 | 100 | 100 | 100 | 100 | 100 | 100 | 100 | 100 |
| | | Powder component (% by mass) | 17.9 | 17.9 | 17.9 | 17.9 | 17.9 | 17.9 | 17.9 | 17.9 | 17.9 |
| | | (C1):(C2) | 6:1 | 25:1 | 4:1 | 4:1 | 1.5:1 | 30:1 | 10:1 | 10:1 | 10:1 |

TABLE 4

|  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| (A) Powder component | (A1) | NAI-treated titanium oxide | — | — | 6.5 | 6.5 | 6.5 | 6.5 | 6.5 |
|  |  | NAI-treated yellow iron oxide | — | — | 1.2 | 1.2 | 1.2 | 1.2 | 1.2 |
|  |  | NAI-treated red iron oxide | — | — | 0.16 | 0.16 | 0.16 | 0.16 | 0.16 |
|  |  | Titanium oxide | 6.5 | — | — | — | — | — | — |
|  |  | Yellow iron oxide | 1.2 | — | — | — | — | — | — |
|  |  | Red iron oxide | 0.16 | — | — | — | — | — | — |
|  |  | Dimethicone-treated titanium oxide | — | 6.5 | — | — | — | — | — |
|  |  | Dimethicone-treated yellow iron oxide | — | 1.2 | — | — | — | — | — |
|  |  | Dimethicone-treated red iron oxide | — | 0.16 | — | — | — | — | — |
|  |  | Stearic acid-treated microparticulate titanium oxide | 10.0 | 10.0 | 10.0 | 10.0 | 10.0 | 10.0 | 10.0 |
| (B) Water-soluble thickener |  | (Al/Mg) silicate | 3.6 | 3.6 | — | 3.6 | 1.0 | 3.6 | 3.6 |
|  |  | Xanthan gum | 0.9 | 0.9 | — | 0.9 | 0.25 | 0.9 | 0.9 |
|  |  | Copolymer-1 | — | — | — | — | 0.5 | — | — |
| (C) Surfactant | (C1) | Glyceryl stearate | 1.0 | 1.0 | 1.0 | — | 1.0 | — | — |
|  | (C2) | Hydrogenated lecithin | 0.3 | 0.3 | 0.3 | 0.3 | — | 0.3 | 0.3 |
|  |  | Sorbitan isostearate | — | — | — | — | — | 1.0 | — |
|  |  | Sorbitan sesquioleate | — | — | — | — | — | — | 1.0 |
| (D) Oily component |  | Cetyl ethylhexanoate | 14.5 | 14.5 | 14.5 | 14.5 | 14.5 | 14.5 | 14.5 |
|  |  | Water | Balance | Balance | Balance | Balance | Balance | Balance | Balance |
|  |  | 1,3-Butylene glycol | 3 | 3 | 3 | 3 | 3 | 3 | 3 |
|  |  | pH adjusting agent | Proper quantity | Proper quantity | Proper quantity | Proper quantity | Proper quantity | Proper quantity | Proper quantity |
|  |  | Antiseptic agent | Proper quantity | Proper quantity | Proper quantity | Proper quantity | Proper quantity | Proper quantity | Proper quantity |
|  |  | Total (parts by mass) | 100 | 100 | 100 | 100 | 100 | 100 | 100 |
|  |  | Powder component (% by mass) | 17.9 | 17.9 | 17.9 | 17.9 | 17.9 | 17.9 | 17.9 |
|  |  | (C1):(C2) | 3.33:1 | 3.33:1 | 3.33:1 | 3.33:1 | 3.33:1 | 3.33:1 | 3.33:1 |

TABLE 5

|  | Example 1 | Example 2 | Example 3 | Example 4 | Example 5 | Example 6 | Example 7 | Example 8 |
|---|---|---|---|---|---|---|---|---|
| Color difference between appearance color and coating film | A | B | B | A | A | B | B | A |
| Color difference after contact with water | A | A | A | A | B | A | B | B |
| Water resistance (contact angle) | A | A | A | A | B | A | A | A |
| Usability  Cover power | A | A | B | A | A | A | A | A |
| Satisfactory spreading | A | B | A | A | A | A | B | A |
| Absence of unevenness | A | B | A | A | A | A | A | A |
| Storage stability | A | A | A | A | A | A | A | A |

|  | Example 9 | Example 10 | Example 11 | Example 12 | Example 13 | Example 14 | Example 15 | Example 16 |
|---|---|---|---|---|---|---|---|---|
| Color difference between appearance color and coating film | A | B | B | A | A | B | B | A |
| Color difference after contact with water | B | B | B | B | B | A | A | B |
| Water resistance (contact angle) | A | A | A | A | A | A | A | A |
| Usability  Cover power | A | A | A | A | A | A | B | A |
| Satisfactory spreading | A | A | A | B | B | B | A | A |
| Absence of unevenness | A | A | A | B | B | B | A | A |
| Storage stability | A | A | A | A | A | A | A | A |

|  | Example 17 | Example 18 | Example 19 | Example 20 | Example 21 | Example 22 | Example 23 | Example 24 |
|---|---|---|---|---|---|---|---|---|
| Color difference between appearance color and coating film | B | A | A | A | B | A | A | A |
| Color difference after contact with water | B | B | B | A | B | B | B | B |

TABLE 5-continued

| | | | | | | | | |
|---|---|---|---|---|---|---|---|---|
| Water resistance (contact angle) | A | A | A | A | B | A | A | A |
| Usability  Cover power | A | A | A | A | B | A | A | A |
| Satisfactory spreading | B | B | B | B | B | B | A | A |
| Absence of unevenness | A | A | B | B | A | A | A | A |
| Storage stability | A | A | A | A | A | A | A | A |

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Color difference between appearance color and coating film | A | D | D | D | D | D | D |
| Color difference after contact with water | C | A | C | C | B | B | B |
| Water resistance (contact angle) | C | A | A | C | A | A | A |
| Usability  Cover power | C | A | A | C | A | A | A |
| Satisfactory spreading | A | C | A | A | A | A | A |
| Absence of unevenness | C | D | D | D | D | D | D |
| Storage stability | A | B | B | B | B | B | B |

Example 25: Blusher

| (Component) | (Blending proportion (% by mass)) |
|---|---|
| 1. NAI-treated titanium oxide | 5.0 |
| 2. NAI-treated yellow iron oxide | 0.8 |
| 3. NAI-treated red iron oxide | 0.1 |
| 4. NAI-treated black iron oxide | 0.01 |
| 5. Red 226 | 0.15 |
| 6. Mica | 3.0 |
| 7. Titanated mica | 4.0 |
| 8. Glass powder | 2.0 |
| 9. Diisostearyl malate | 5.0 |
| 10. Triethylhexanoin | 10 |
| 11. Glyceryl stearate (HLB 3) | 1.0 |
| 12. Polysorbate 80 (HLB 15) | 0.2 |
| 13. Silica | 3.0 |
| 14. Polymethyl methacrylate | 5.0 |
| 15. Copolymer-1 | 0.5 |
| 16. (Al/Mg) silicate | 0.5 |
| 17. 1,3-Butylene glycol | 3.0 |
| 18. Glycerin | 2.0 |
| 19. Antiseptic agent | Proper quantity |
| 20. pH adjusting agent | Proper quantity |
| 21. Water | Balance |

The details of the above-described components are as previously described above.

<Production Method>

Components 1 to 8, 13, and 14 were heated and mixed at 90° C., and an oil phase was obtained. Next, components 9 to 12 and 15 to 21 were heated and mixed at 90° C., and an aqueous phase was obtained. The oil phase was mixed with the aqueous phase under stirring to be emulsified, and the resultant was cooled to obtain an oil-in-water type emulsified cosmetic (blusher).

<Evaluation>

The obtained blusher was subjected to evaluations similar to those described above, and it was confirmed that the following evaluation results were obtained: the color difference between the appearance color and the coating film "A", the color difference after contact with water "A", water resistance (contact angle) "A", color development (evaluated instead of cover power) "A", satisfactory spreading "B", absence of unevenness "B", and storage stability "A".

Example 26: Eyeshadow

| (Component) | (Blending proportion (% by mass)) |
|---|---|
| 1. NAI-treated synthetic phlogopite | 8.0 |
| 2. NAI-treated titanated mica | 4.0 |
| 3. NAI-treated iron oxide-coated titanated mica | 6.0 |
| 4. Glass powder | 2.0 |
| 5. Diisostearyl malate | 2.0 |
| 6. Cetyl ethylhexanoate | 10 |
| 7. Glyceryl stearate (HLB 3) | 1.0 |
| 8. Hydrogenated lecithin | 0.3 |
| 9. Silica | 3.0 |
| 10. Xanthan gum | 0.8 |
| 11. (Al/Mg) silicate | 0.5 |
| 12. 1,3-Butylene glycol | 3.0 |
| 13. Glycerin | 2.0 |
| 14. Antiseptic agent | Proper quantity |
| 15. pH adjusting agent | Proper quantity |
| 16. Water | Balance |

The details of the above-described components are as previously described above.

<Production Method>

Components 1 to 8 were heated and mixed at 90° C., and an oil phase was obtained. Next, components 9 to 16 were heated and mixed at 90° C., and an aqueous phase was obtained. The oil phase was mixed with the aqueous phase under stirring to be emulsified, and the resultant was cooled to obtain an oil-in-water type emulsified cosmetic (eyeshadow).

<Evaluation>

The obtained eyeshadow was subjected to evaluations similar to those described above, and it was confirmed that the following evaluation results were obtained: the color difference between the appearance color and the coating film "A", the color difference after contact with water "A", water resistance (contact angle) "A", color development (evaluated instead of cover power) "A", satisfactory spreading "A", absence of unevenness "A", and storage stability "A".

Example 27: Sunscreen

| (Component) | (Blending proportion (% by mass)) |
| --- | --- |
| 1. NAI-treated microparticulate titanium oxide | 15.0 |
| 2. NAI-treated yellow iron oxide | 0.4 |
| 3. NAI-treated red iron oxide | 0.1 |
| 4. NAI-treated black iron oxide | 0.01 |
| 5. Methyltrimethicone | 5.0 |
| 6. Dimethicone | 10 |
| 7. Glyceryl stearate (HLB 3) | 2.0 |
| 8. Polysorbate 80 (HLB 15) | 0.2 |
| 9. Hydrogenated lecithin | 0.5 |
| 10. Silica | 3 |
| 11. Copolymer-1 | 0.7 |
| 12. Xanthan gum | 0.3 |
| 13. 1,3-Butylene glycol | 3.0 |
| 14. Glycerin | 2.0 |
| 15. Antiseptic agent | Proper quantity |
| 16. pH adjusting agent | Proper quantity |
| 17. Water | Balance |

The details of the above-described components are as previously described above.

<Production Method>

Components 1 to 7 were heated and mixed at 90° C. to obtain an oil phase, and next, components 8 to 17 were heated and mixed at 90° C. to obtain an aqueous phase. The oil phase was mixed with the aqueous phase under stirring to be emulsified, and the resultant was cooled to obtain an oil-in-water type emulsified cosmetic (sunscreen).

<Evaluation>

The obtained sunscreen was subjected to evaluations similar to those described above, and it was confirmed that the following evaluation results were obtained: the color difference between the appearance color and the coating film "A", the color difference after contact with water "A", water resistance (contact angle) "A", satisfactory spreading "A", absence of unevenness "A", and storage stability "A".

What is claimed is:

1. An oil-in-water type emulsified cosmetic comprising:
(A) a powder, (B) a water-soluble thickener, and (C) a surfactant,
wherein the content of the component (A) is 1% to 30% by mass based on the total amount of the cosmetic,
the component (A) contains (A1) an N-acyl acidic amino acid-treated powder,
the component (C) contains (C1) a solid nonionic surfactant having a hydrophile-lipophile balance (HLB) value of less than 7 and (C2) a surfactant having an HLB value of 7 or greater, and
the mass ratio (C1):(C2) between the component (C1) and the component (C2) is 1.5:1 to 30:1.

2. The oil-in-water type emulsified cosmetic according to claim 1, wherein the inorganic-organic balance (IOB) value of a treatment agent for the powder in the component (A1) is 2 to 5.

3. The oil-in-water type emulsified cosmetic according to claim 1, further comprising (C2-1) a nonionic surfactant having an HLB value of 7 or greater as the component (C2).

4. The oil-in-water type emulsified cosmetic according to claim 1, further comprising (C2-2) hydrogenated lecithin as the component (C2).

5. The oil-in-water type emulsified cosmetic according to claim 1, wherein the content of the component (A1) is 1% by mass or more based on the total amount of the cosmetic, the content of the component (B) is 0.01% to 5% by mass based on the total amount of the cosmetic, and the content of the component (C) is 0.1% to 9% by mass based on the total amount of the cosmetic.

6. The oil-in-water type emulsified cosmetic according to claim 5, further comprising (D) an oily component,
wherein the content of the component (D) is 1% to 40% by mass based on the total amount of the cosmetic.

7. The oil-in-water type emulsified cosmetic according to claim 1, wherein the component (B) contains two or more selected from the group consisting of a (Na acrylate-Na acryloyldimethyl taurine) copolymer, xanthan gum, and (Al/Mg) silicate.

8. The oil-in-water type emulsified cosmetic according to claim 1, wherein the cosmetic substantially does not comprise a component having a polyethylene glycol (PEG) group.

9. The oil-in-water type emulsified cosmetic according to claim 1, wherein the viscosity at 25° C. is 500 to 300000 mPa·s.

* * * * *